United States Patent [19]

Knaus et al.

[11] Patent Number: 4,771,057

[45] Date of Patent: Sep. 13, 1988

[54] REDUCED PYRIDYL DERIVATIVES WITH CARDIOVASCULAR REGULATING PROPERTIES

[75] Inventors: Edward E. Knaus; Michael W. Wolowyk; Lina Dagnino; Moy C. Li-Kwong-Ken, all of Edmonton; Donald A. Soboleski, Drumheller; Hla Wynn, Edmonton, all of Canada

[73] Assignee: University of Alberta, Alberta, Canada

[21] Appl. No.: 824,920

[22] Filed: Feb. 3, 1986

[51] Int. Cl.$^4$ ............... A61K 31/44; C07D 401/04
[52] U.S. Cl. .................... 514/334; 514/344; 514/352; 514/354; 546/257; 546/286; 546/287; 546/304; 546/307; 546/312; 546/321
[58] Field of Search ............ 546/257, 286, 287, 307, 546/304, 312, 321; 514/334, 344, 352, 354

[56] References Cited

U.S. PATENT DOCUMENTS

| | | | |
|---|---|---|---|
| 3,488,359 | 1/1970 | Bossert et al. | 546/257 |
| 3,773,773 | 11/1973 | Bossert | 546/257 |
| 3,799,934 | 3/1974 | Meyer et al. | 546/257 |
| 3,883,543 | 5/1975 | Bossert | 546/321 |
| 3,933,834 | 1/1976 | Meyer et al. | 546/321 |
| 3,956,341 | 5/1976 | Loev | 546/321 |
| 3,985,758 | 10/1976 | Murakami et al. | 546/321 |
| 4,021,434 | 5/1977 | Murakami et al. | 546/321 |
| 4,048,171 | 9/1977 | Bossert et al. | 546/257 |
| 4,248,873 | 2/1987 | Bossert et al. | 546/257 |
| 4,393,070 | 7/1983 | Sato et al. | 546/321 |
| 4,467,093 | 8/1984 | Jenko et al. | 546/321 |
| 4,497,808 | 2/1985 | Zimmermann et al. | 546/257 |
| 4,510,310 | 4/1985 | Wehinger et al. | 546/257 |

FOREIGN PATENT DOCUMENTS

| | | |
|---|---|---|
| 3130041 | 2/1983 | Fed. Rep. of Germany . |
| 3208628 | 9/1983 | Fed. Rep. of Germany . |
| 3433239 | 11/1984 | Fed. Rep. of Germany . |
| 0031663 | 2/1982 | Japan . |

OTHER PUBLICATIONS

Tacke, R. et al., Eur. J. Med. Chem. 18: 155-161, 1983.
Dagnino et al., J. Med. Chem., 1987, pp. 640-646.
Thomas et al., J. Cardiovascular Pharmacy, 6: 1170-1176, 1984.
CA 100: 67624h, Baumane et al.
CA 98: 34471t, Muceniece.
CA 70: 87580f, Bossert et al.
Loev, B. et al., J. Med. Chem. 17: 956-965, 1974.
Lusis et al., Chem. Het. cpds. 19, pp. 415-419, 1983.
Mutsenietse, Chem. Het. cpds. 18: 942-945, 1982.

Primary Examiner—Jane T. Fan
Attorney, Agent, or Firm—Sughrue, Mion, Zinn, Macpeak & Seas

[57] ABSTRACT

Pharmaceutical compounds of the general formula (1):

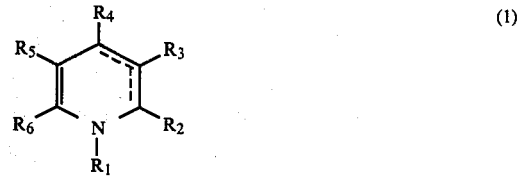

have been prepared and non-toxic pharmaceutically acceptable salts thereof, wherein the ring system is a 1,2- or 1,4-dihydropyridyl radical; $R_1$ is a hydrogen, lower alkyl, lower alkyl carbonyl or lower alkoxy carbonyl substituent; $R_2$ is a lower alkly or phenyl substituent; $R_3$ is a lower alkoxy carbonyl, (N,N-lower dialkylamino) lower alkoxy carbonyl, (N-lower alkyl-N-phenyl lower alkyl amino) lower alkoxy carbonyl, lower alkoxy lower alkoxy carbonyl, nitro, or cyano substituent; $R_4$ is a member selected from the group consisting of pyridyl, N-lower alkoxy carbonyl-1,2-dihydropyridyl, N-lower alkyl carbonyl-1,2-dihydropyridyl, N-phenyloxy carbonyl-1,2-dihydropyridyl, N-lower alkoxy carbonyl-1,6-dihydropyridyl, N-lower alkyl carbonyl-1,6-dihydropyridyl, N-lower alkyl carbonyl-1,6-dihydropyridyl, N-phenyloxy carbonyl-1,6-dihydropyridyl, N-lower alkoxy carbonyl-1,4-dihydropyridyl, N-lower alkyl carbonyl-1,4-dihydropyridyl, N-phenyloxy carbonyl-1,4-dihydropyridyl, N-lower alkyl 1,2,3,6-tetrahydropyridyl, N-lower alkoxy carbonyl-1,2,3,6-tetrahydropyridyl, N-lower alkyl carbonyl-1,2,3,6-tetrahydropyridyl, nitro substituted phenyl or trifluoromethyl substituted phenyl; $R_5$ is a lower alkoxy carbonyl, (N,N-lower dialkylamino) lower alkoxy carbonyl, (N-lower alkyl-N-phenyl lower alkyl amino) lower alkoxy carbonyl, lower alkoxy lower alkoxy carbonyl, nitro, or cyano substituent; $R_6$ is a lower alkyl, or phenyl substituent, lower denoting a straight or branched chain having from 1-6 carbon atoms. These compounds regulate cardiovascular activity due to their ability to induce cerebral and peripheral vasodilation, decrease heart rate, and/or increase cardiac contractility, and are useful in the treatment of angina, arrhythmias, cerebralvascular disease and hypertension.

61 Claims, No Drawings

REDUCED PYRIDYL DERIVATIVES WITH CARDIOVASCULAR REGULATING PROPERTIES

FIELD OF INVENTION

The present invention relates to pharmaceutical compounds. More particularly, the invention provides novel reduced pyridyl derivatives or non-toxic pharmaceutically acceptable salts thereof having useful physiological effects, particularly cardiovascular regulating properties. The invention relates to such compounds and compositions thereof, and to processes for making and using them.

DESCRIPTION OF THE INVENTION

The novel reduced pyridyl derivatives have been prepared which have the structural formula (1):

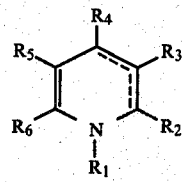
(1)

and non-toxic pharmaceutically acceptable salts thereof, wherein the ring system is a 1,2-or 1,4dihydropyridyl radical; $R_1$ is a hydrogen, lower alkyl, lower alkyl carbonyl or lower alkoxy carbonyl substituent; $R_2$ is a lower alkyl or phenyl substituent; $R_3$ is a lower alkoxy carbonyl, (N,N-lower dialkylamino) lower alkoxy carbonyl, (N-lower alkyl-N-phenyl lower alkyl amino) lower alkoxy carbonyl, lower alkoxy lower alkoxy carbonyl, nitro or cyano substituent; $R_4$ is a member selected from the group consisting of pyridyl, N-lower alkoxy carbonyl-1,2-dihydropyridyl, N-lower alkyl carbonyl-1,2-dihydropyridyl, N-phenyloxy carbonyl-1,6-dihydropyridyl, N-lower alkoxy carbonyl-1,4-dihydropyridyl, N-lower alkyl carbonyl-1,4-dihydropyridyl, N-phenyloxy carbonyl-1,4-dihydropyridyl, N-lower alkyl 1,2,3,6-tetrahydropyridyl, N-lower alkoxy carbonyl-1,2,3,6-tetrahydropyridyl, N-lower alkyl carbonyl-1,2,3,6-tetrahydropyridyl, nitro substituted phenyl or trifluoromethyl substituted phenyl; $R_5$ is a lower alkoxy carbonyl, (N,N-lower dialkylamino) lower alkoxy carbonyl, (N-lower alkyl-N-phenyl lower alkyl amino) lower alkoxy carbonyl, lower alkoxy lower alkoxy carbonyl, nitro, or cyano substituent; $R_6$ is a lower alkyl, or phenyl substituent. In this specification, it will be understood that "lower alkyl" and "lower alkoxy" substituents mean those having from 1-6 carbon atoms. Compounds of formula (1) wherein the ring system is a 1,4-dihydropyridyl radical, the $R_3$ and $R_5$ substituents are different, have an asymmetric carbon at the C-4 position and therefore exist as a racemic mixture. Compounds of formula (1) wherein the ring system is a 1,2-dihydropyridyl radical always have an asymmetric carbon at the C-2 position and exist as a racemic mixture. In this specification, it will be understood that compounds of formula (1) having an asymmetric carbon at the C-4 or C-2 position as described exist as racemates. These compounds exhibit cardiovascular regulating activity. Non-toxic pharmaceutically acceptable salts are also within the scope of the present invention.

These 3-lower alkyl-5-methyl 2,6-dimethyl-4-(pyridyl)-1,4-dihydropyridine-3,5-dicarboxylates are prepared by reacting in an inert solvent, an alkyl acetoacetate of the formula (2):

$$CH_3COCH_2R_3 \qquad (2)$$

wherein $R_3$ is a member selected from the group consisting of lower alkoxy carbonyl, (N,N-lower dialkylamino) lower alkoxy carbonyl, (N-lower alkyl-N-phenyl lower alkyl amino) lower alkoxy carbonyl and lower alkoxy lower alkoxy carbonyl, with methyl-3-aminocrotonate of the formula (3):

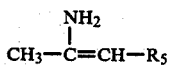
(3)

wherein $R_5$ is a methoxycarbonyl substituent and a carboxaldehyde of formula (4):

$$R_4\text{—CHO} \qquad (4)$$

wherein $R_4$ is a pyridyl substituent, allowing the reaction to occur (normally at reflux temperature) to convert to 3-lower alkyl-5-methyl 2,6-dimethyl-4-(pyridyl)-1,4-dihydropyridine-3,5-dicarboxylates of formula (5):

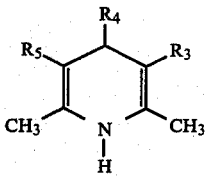
(5)

wherein $R_3$, $R_4$ and $R_5$ are as defined above. These reactions can take place in inert organic solvents, such as ethanol, ether, tetrahydrofuran, chloroform, benzene, toluene, hexane, etc.

The related lower 3,5-dialkyl 2,6-dimethyl-4-(pyridyl)-1,4-dihydropyridine 3,5-dicarboxylates are prepared by reacting in an inert solvent as stated above, two equivalents of the alkyl acetoacetate of formula (2), wherein $R_3$ is defined as above with a carboxaldehyde of formula (4), wherein $R_4$ are as defined above and ammonium hydroxide, allowing the reaction to occur (normally at reflux temperature) to convert to lower 3,5-dialkyl 2,6-dimethyl-4-(pyridyl)-1,4-dihydropyridine-3,5-dicarboxylates of formula (5) wherein $R_3$ and $R_5$ are both as fined for $R_3$ above, and $R_4$ is a pyridyl substituent.

The lower alkyl 3-cyano-2,6-dimethyl-4-(pyridyl)-1,4-dihydropyridine-5-carboxylates are prepared by reacting in an inert solvent, as stated above, 3-aminocrotonitrile of formula (6):

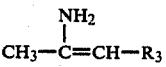
(6)

wherein $R_3$ *is a cyano substituent with a lower alkyl* 3-aminocrotonate of formula (3) wherein $R_5$ is a member selected from the group consisting of a lower alkoxy carbonyl, (N,N-lower dialkylamino) lower alkoxy carbonyl, (N-lower alkyl-N-phenyl lower alkyl amino) lower alkoxy carbonyl, lower alkoxy lower alkoxy carbonyl and a carboxaldehyde of formula (4), wherein $R_4$ is a pyridyl substituent, allowing the reaction to occur (normally at reflux temperature) to convert to lower alkyl 3-cyano- 2,6-dimethyl-4-(pyridyl)-1,4-dihydropyridine-5-carboxylates of formula (5), wherein $R_3$, $R_4$ and $R_5$ are as defined above.

The related 3,5-dicyano-2,6-dimethyl-4-(pyridyl)-1,4-dihydropyridines are prepared by reacting in an inert solvent, as stated above, two equivalents of 3-aminocrotonitrile of formula (6), wherein $R_3$ is a cyano substituent with a carboxyaldehyde of formula (4), wherein $R_4$ is a pyridyl substituent, allowing the reaction to occur (normally at reflux temperature) to convert to 3,5-dicyano-2,6-dimethyl-4-(pyridyl)-1,4-dihydropyridines of formula (5), wherein $R_3$ and $R_5$ are cyano substituents and $R_4$ is defined as above.

The lower alkyl 2,6-dimethyl-3-nitro-4-(pyridyl)-1,4-dihydropyridine-5-carboxylates are prepared by reacting in an inert solvent, as stated above, a lower alkyl 3-aminocrotonate of formula (3), wherein $R_5$ is a member of the group consisting of a lower alkoxy carbonyl, (N,N-lower dialkylamino) lower alkoxy carbonyl, (N-lower alkyl-N-phenyl lower alkyl amino) lower alkoxy carbonyl, lower alkoxy lower alkoxy carbonyl substituent, with 1-nitro-2-propanone of formula (2), wherein $R_3$ is a nitro substituent and a carboxaldehyde of formula (4), wherein $R_4$ is a pyridyl substituent, allowing the reaction to occur (normally at reflux temperature) to convert to lower alkyl 2,6-dimethyl-3-nitro-4-(pyridyl)-1,4-dihydropyridine-5-carboxylates of formula (5), wherein $R_3$, $R_4$ and $R_5$ are as defined above.

The 1,2,3,5,6-pentasubstituted-4-(N-alkoxycarbonyl-1',2'-dihydropyridyl)-1,4-dihydropyridines and 1,2,3,5,6-pentasubstituted-4-(N-alkoxycarbonyl-1',6'-dihydropyridyl)-1,4-dihydropyridines are prepared by reacting in an inert solvent, a 1,2,3,5,6-pentasubstituted-4-(pyridyl)-1,4-dihydropyridine of formula (7):

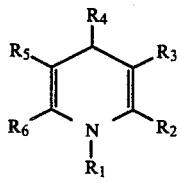

(7)

wherein $R_1$ is a member selected from the group consisting of hydrogen, lower alkyl, lower alkyl carbonyl or lower alkoxy carbonyl; $R_2$ and $R_6$ are members selected from the group consisting of lower alkyl and phenyl; $R_3$ and $R_5$ are members selected from the group consisting of lower alkoxy carbonyl, lower alkoxy lower alkoxy carbonyl, nitro and cyano; $R_4$ is a pyridyl substituent, with a chloroformate of formula (8):

$R_7OOCCl$ (8)

wherein $R_7$ is a member selected from the group consisting of lower alkyl, phenyl, lower alkyl substituted phenyl, lower alkoxy substituted phenyl and halogen substituted phenyl, in the presence of a suitable reducing agent converting to the corresponding 1,2,3,5,6-pentasubstituted-4-(N-alkoxycarbonyl-1',2'-dihydropyridyl)-1,4-dihydropyridine derivatives of formula (9):

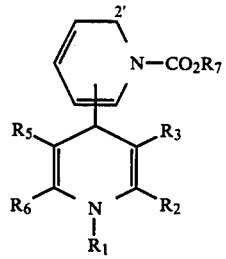

(9)

wherein $R_1$, $R_2$, $R_3$, $R_5$, $R_6$ and $R_7$ are defined as above, and 1,2,3,5,6-pentasubstituted-4-(N-alkoxycarbonyl-1',6'-dihydropyridyl)-1,4-dihydropyridine derivatives of formula (10):

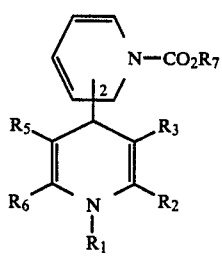

(10)

wherein $R_1$, $R_2$, $R_3$, $R_5$, $R_6$ and $R^7$ are as defined above. These reactions can take place in inert organic solvents, such as methanol, ethanol, tetrahydrofuran, etc. preferably at $-65°$ C.

The 1,2,3,5,6-pentasubstituted-4-(N-lower alkyl-1',2',3',6'-tetrahydropyridyl)-1,4-dihydropyridines are prepared by reacting in an inert solvent such as acetone, a 1,2,3,5,6-pentasubstituted-4-(pyridyl)-1,4-dihydropyridine of formula (7) wherein $R_1$ is a member selected from the group consisting of hydrogen, lower alkyl, lower alkyl carbonyl or lower alkoxy carbonyl; $R_2$ and $R_6$ are members selected from the group consisting of lower alkyl and phenyl; $R_3$ and $R_5$ are members selected from the group consisting of low alkoxy carbonyl, lower alkoxy lower alkoxy carbonyl, nitro and cyano; $R_4$ is a pyridyl substituent, with a lower alkyl iodide of formula (11):

$R_7—I$ (11)

wherein $R_7$ is a lower alkyl substituent, and heating sufficiently to convert to the N-lower alkyl pyridinium iodide salt of formula (12):

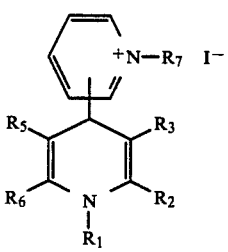

(12)

wherein $R_1$, $R_2$, $R_3$, $R_5$, $R_6$ and $R_7$ are as defined above, and converting the N-lower alkyl pyridinium salt in the presence of a suitable reducing agent such as sodium borohydride to the corresponding 1,2,3,5,6-pentasubstituted-4-(N-lower alkyl-1′,2′,3′,6′-tetrahydropyridyl)-1,4-dihydropyridine derivatives of formula (13):

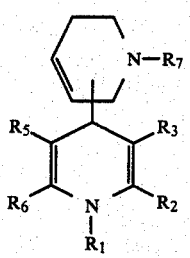
(13)

wherein $R_1$, $R_2$, $R_3$, $R_5$, $R_6$ and $R_7$ are as defined above. This reaction can take place in an inert organic solvent as aqueous ethanol.

The 1,2,3,5,6-pentasubstituted-4-(substituted phenyl)-1,2-dihydropyridines are prepared by reacting in an inert solvent such as ethanol, an aldehyde of formula (14):

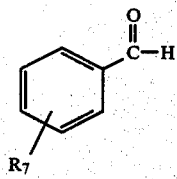
(14)

wherein $R_7$ is a member selected from a group consisting of lower alkyl, low alkoxy, halogen, nitro and trifluoromethyl, with a lower alkyl acetoacetate of formula (15):

$$R_2(R_6)COCH_2R_3(R_5) \quad (15)$$

wherein $R_2$ and $R_6$ are members selected from the group consisting of lower alkyl, phenyl, lower alkyl substituted phenyl, lower alkoxy substituted phenyl and halogen substituted phenyl; $R_3$ and $R_5$ are members selected from the group consisting of lower alkoxy carbonyl and lower alkoxy lower alkoxy carbonyl, and ammonium hydroxide, allowing the reaction to occur (normally at reflux temperature) to convert to a 1,4-dihydropyridine derivative of formula (16):

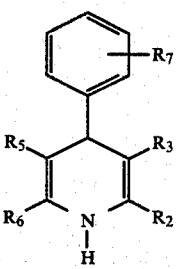
(16)

wherein $R_2$, $R_3$, $R_5$, $R_6$ and $R_7$ are as defined above. Oxidation of the 1,4-dihydropyridine of formula (16), wherein $R_2$, $R_3$, $R_5$, $R_6$ and $R_7$ are as defined above, in the presence of a suitable oxidizing agent as sodium nitrate in an inert solvent as glacial acetic acid, allowing the reaction to occur to convert to an aromatic pyridine of formula (17):

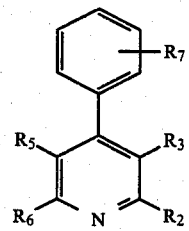
(17)

wherein $R_2$, $R_3$, $R_5$, $R_6$ and $R_7$ are as defined above, alkylation of the pyridine of formula (17) wherein $R_2$, $R_3$, $R_5$, $R_6$ and $R_7$ are as defined above, in the presence of a suitable lower dialkyl sulfate of formula (18):

$$(R_1)_2SO_4 \quad (18)$$

wherein $R_1$ is a lower alkyl substituent, in an inert solvent (normally at reflux temperature), allowing the reaction to occur to convert to a N-lower alkyl pyridinium lower alkyl sulfate salt of formula (19):

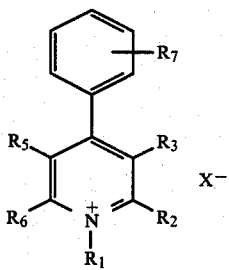
(19)

wherein $R_1$ is a lower alkyl substituent, X is a lower alkyl sulfate anion, and $R_2$, $R_3$, $R_5$, $R_6$ and $R_7$ are as defined above. Treatment of the N-lower alkyl pyridinium lower alkyl sulfate salt of formula (19) wherein $R_1$, $R_2$, $R_3$, $R_5$, $R_6$, $R_7$ and $X^-$ are as defined above, with aqueous sodium perchlorate, allowing the reaction to occur at room temperature to convert to N-lower alkyl perchlorate salt of formula (19) wherein $X^-$ is a perchlorate anion. Reduction of the N-lower alkyl pyridinium perchlorate salt of formula (19) wherein $R_1$, $R_2$, $R_3$, $R_5$, $R_6$ and $R_7$ are as defined above in the presence of a suitable reducing agent as sodium borohydride in an inert solvent such as aqueous ethanol, allowing the reaction to occur (normally at 25° C.) to convert to a 1,2-dihydropyridine derivative of formula (20):

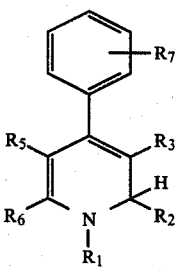
(20)

wherein $R_1$, $R_2$, $R_3$, $R_5$, $R_6$ and $R_7$ are as defined above.

More particularly, the compounds listed in Tables 1-6 have been prepared and through testing, have been found to have calcium channel antagonist antihypertensive activity (Table 7).

More particularly the 4-(3'-pyridyl) and 4-(4'-pyridyl) analogs of methyl-2,6,-dimethyl-3-nitro-1,4-dihydropyridine-5-carboxylate have been prepared and through testing have been found to possess calcium channel agonist activity by stimulating muscle contraction and increasing heart rate.

Suitable pharmaceutically acceptable salt forms of these compounds include alkaline metal salts, for example, the potassium or sodium salt, and the ammonium salt, and alkaline earth metal salts, e.g. the calcium or Mg salt, as well as the mineral acid salts, for example, the hydrochloride and hydrobromide salts.

These compounds can be administered either parenterally, as by injection, or orally. As a liquid carrier, a carrier such as water, ethyl alcohol or polyethylene glycol, or other physiologically acceptable solvents or dispersing liquids can be used. For oral administration, either solid or liquid carriers may be used. One commonly used solid carrier is gum acacia, but others are also suitable. An operative dosage range is between about 0.01 and 200 mg/kg, preferably between 0.1 and 10 mg/kg.

The following non-limitative examples illustrate some selective methods for producing the compounds according to the present invention, as well as comparative data illustrating the calcium channel antagonist or calcium channel agonist effect of representative compounds according to the present invention.

The starting materials for the preparative of compounds of formula (1), viz the acetoacetate of formula (2), 3-aminocrotonates of formula (3), aldehydes of formula (4), 3-aminocrotonitrile of formula (6), chloroformates of formula (8), alkyl iodides of formula (11), acetoacetates of formula (15) and dialkyl sulfates of formula (18) are either known or are conveniently prepared from known starting materials from methods known per se.

PREPARATION

Example 1

3,5-dimethyl 2,6-dimethyl-4-(2¹-pyridyl)-1,4-dihydropyridine-3,5-dicarboxylate (D-1)

(See schematic representation of reaction)

Methyl acetoacetate (0.1 mol) was added to a solution of 2-pyridinecarboxaldehyde (10.7 g, 0.1 mol) in ethanol (50 mL) and then methyl-3-aminocrotonate (8.9 g, 0.1 mol) was added with stirring. The reaction mixture was heated at reflux for 16 h and then poured onto crushed ice (100 mL). The crude product was separated from the mixture by filtration and the aqueous fraction was extracted with dichloromethane. The combined organic extracts were dried ($MgSO_4$) and the solvent removed in vacuo. The combined solids were purified by elution from a silica gel column using ethyl acetate-acetone (9:1 v/v) as eluant to give 3,5-dimethyl 2,6-dimethyl-4-(2'-pyridyl)-1,4-dihydropyridine-3,5-dicarboxylate (77%) as a white solid with mp 239°–241° C.; IR ($CHCl_3$) 3224 (NH) and 1704 ($CO_2$) cm$^{-1}$; NMR (DMSO-$d_6$) 2.3 (s, 6H, Me), 3.7 (s, 6H, $CO_2Me$), 5.23 (s, 1H, H-4), 7.1–7.8 (m, 3H, H-3', H-4', H-5'), 8.6 (m, 1H, H-6'), 8.9 (s, 1H, NH, exchanges with deuterium oxide). Analysis found: C, 63.72; H, 6.27; N, 9.5. $C_{16}H_{18}N_2O_4$ requires: C, 63.58; H, 5.96; N, 9.27.

Schematic for Example 1

$$CH_3COCH_2CO_2CH_3 + CH_3-\underset{(3)}{\overset{\overset{NH_2}{|}}{C}}=CH-CO_2CH_3 +$$
(2)

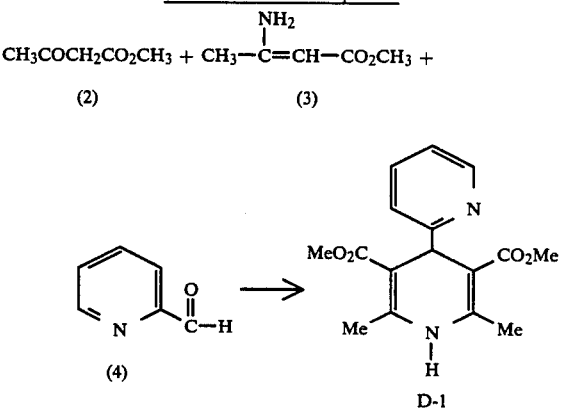

Example 2

Related 3-alkyl-5-methyl 2,6-dimethyl-4-(pyridyl)-1,4-dihdyropyridine-3,5-dicarboxylate derivatives have been prepared as shown in the schematic representation shown below using equivalent quantities of other alkyl acetoacetates of formula (2), 3-aminocrotonates of formula (3) and aldehydes of formula (4) using a procedure similar to that outlined in Example 1. The melting point for each product is set out in Table 1.

Schematic for Example 2

$$CH_3COCH_2R_3 + CH_3-\underset{(3)}{\overset{\overset{NH_2}{|}}{C}}=CH-CO_2CH_3 +$$
(2)

$$R_4-CHO \longrightarrow$$
(4)

[structure of product (5): MeO₂C, R₄, R₃, Me, N-H, Me substituted dihydropyridine]

TABLE 1

3-alkyl-5-methyl 2,6-dimethyl-4-(pyridyl)-1,4-dihydropyridine-3,5-dicarboxylates prepared according to Example 2.

| Chemical Name | Designation | $R_3$ | $R_4$ | mp |
|---|---|---|---|---|
| 3-Isopropyl-5-methyl 2,6-dimethyl-4-(2'-pyridyl)-1,4-dihydropyridine-3,5-dicarboxylate | D-2 | —$CO_2$—i-Pr | 2-pyridyl | 186–188° |
| 3-Isobutyl-5-methyl 2,6-dimethyl-4-(2'-pyridyl)-1,4-dihydropyridine-3,5-dicarboxylate | D-3 | —$CO_2$—i-Bu | 2-pyridyl | 162–164° |
| 3-[2-(N,N—dimethylamino)ethyl]-5-methyl 2,6-dimethyl-4-(2'-pyridyl)-1,4-dihydropyridine-3,5-dicarboxylate | D-4 | —$CO_2CH_2CH_2NMe_2$ | 2-pyridyl | 183–184° |

TABLE 1-continued 3-alkyl-5-methyl 2,6-dimethyl-4-(pyridyl)-1,4-dihydropyridine-3,5-dicarboxylates prepared according to Example 2.

| Chemical Name | Designation | $R_3$ | $R_4$ | mp |
|---|---|---|---|---|
| 3,5-Dimethyl 2,6-dimethyl-4-(3'-pyridyl)-1,4-dihydropyridine-3,5-dicarboxylate | D-5 | $-CO_2Me$ | 3-pyridyl | 249–250° |
| 3-Isopropyl-5-methyl 2,6-dimethyl-4-(3'-pyridyl)-1,4-dihydropyridine-3,5-dicarboxylate | D-6 | $-CO_2-i-Pr$ | 3-pyridyl | 176–178° |
| 3-Isobutyl-5-methyl 2,6-dimethyl-4-(3'-pyridyl)-1,4-dihydropyridine-3,5-dicarboxylate | D-7 | $-CO_2-i-Bu$ | 3-pyridyl | 180–182° |
| 3-[2-(N,N—dimethylamino)ethyl]-5-methyl 2,6-dimethyl-4-(3'-pyridyl)-1,4-dihydropyridine-3,5-dicarboxylate | D-8 | $-CO_2CH_2CH_2NMe_2$ | 3-pyridyl | 192–194° |
| 3,5-Dimethyl 2,6-dimethyl-4-(4'-pyridyl)-1,4-dihydropyridine-3,5-dicarboxylate | D-9 | $-CO_2Me$ | 4-pyridyl | 190–192° |
| 3-Isopropyl-5-methyl 2,6-dimethyl-4-(4'-pyridyl)-1,4-dihydropyridine-3,5-dicarboxylate | D-10 | $-CO_2-i-Pr$ | 4-pyridyl | 199–200° |
| 3-Isobutyl-5-methyl 2,6-dimethyl-4-(4'-pyridyl)-1,4-dihydropyridine-3,5-dicarboxylate | D-11 | $-CO_2-i-Bu$ | 4-pyridyl | 126–127° |
| 3-[2-(N,N—dimethylamino)ethyl]-5-methyl 2,6-dimethyl-4-(4'-pyridyl)-1,4-dihydropyridine-3,5-dicarboxylate | D-12 | $-CO_2CH_2CH_2NMe_2$ | 4-pyridyl | 144-145° |

Example 3

3,5-diethyl 2,6-dimethyl-4-(2'-pyridyl)-1,4-dihydropyridine-3,5-dicarboxylate (D-13)

(See schematic representation following example)

Ethyl acetoacetate (0.2 mol) was added to a solution of 2-pyridinecarboxaldehyde (10.7 g, 0.1 mol) in ethanol (50 mL), followed by addition of ammonium hydroxide (14 g, 0.4 mol, $NH_3$ solution content 30%) with stirring. The yellow mixture was heated under reflux for 16 h and poured onto crushed ice (100 mL). The crude product was separated from the mixture by filtration and the aqueous fraction was extracted with dichloromethane. The combined organic extracts were dried and the solvent removed in vacuo. The combined solids were purified by elution from a silica gel column using ethyl acetate-acetone (9:1 v/v) as eluant to give 3,5-diethyl 2,6-dimethyl-4-(2'-pyridyl)-1,4-dihydropyridine-3,5-dicarboxylate as a white solid (89%) with mp 194°–195° C.; IR ($CHCl_3$) 3160 (NH) and 1688 ($CO_2$) $cm^{-1}$; NMR (DMSO-$d_6$) 1.12 (t, J=6 Hz, 6H, $CO_2CH_2\overline{CH_3}$), 2.22 (s, 6H, $CH_3$), 4.02 (q, J=6 Hz, 4H, $CO_2\overline{CH_2}CH_3$), 5.02 (s, 1H, H-4), 7.0–7.8 (m, 3H, H-3', H-4', $\overline{H-5'}$), 8.48 (m, 1H, H-6'), 8.8 (s, 1H, NH, exchanges with deuterium oxide). Analysis found: C, 65.36; H, 6.91; N, 8.27. $C_{18}H_{22}N_2O_4$ requires: C, 65.45; H, 6.66; N, 8.48.

Schematic for Example 3

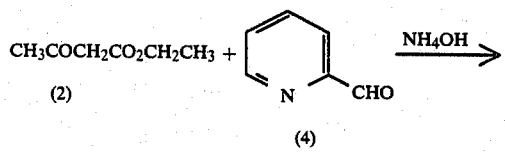

(2)      (4)

-continued
Schematic for Example 3

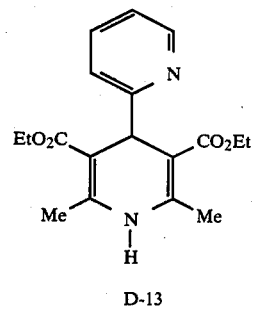

D-13

Example 4

Related dialkyl 2,6-dimethyl-4-(pyridyl)-1,4-dihydropyridine-3,5-dicarboxylate derivatives have been prepared as shown in the schematic representation shown below using equivalent quantities of other alkyl acetoacetates of formula (2) and aldehydes of formula (4) using a procedure similar to that outlined in Example 3.

The melting point of each product is set out in Table 2.

Schematic for Example 4

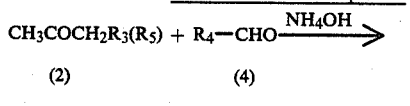

(2)      (4)

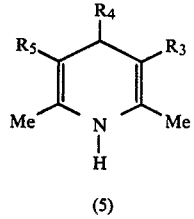

(5)

TABLE 2

Dialkyl 2,6-dimethyl-4-(pyridyl)-1,4-dihydropyridine-3,5-dicarboxylates prepared according to Example 4

| Chemical Name | Designation | $R_3$ and $R_5$ | $R_4$ | mp |
|---|---|---|---|---|
| 3,5-Diisopropyl 2,6-dimethyl-4-(2'-pyridyl)-1,4-dihydropyridine-3,5-dicarboxylate | D-14 | —$CO_2$—i-Pr | 2-pyridyl | 192–193° |
| 3,5-Diisobutyl 2,6-dimethyl-4-(2'-pyridyl)-1,4-dihydropyridine-3,5-dicarboxylate | D-15 | —$CO_2$—i-Bu | 2-pyridyl | 152–153° |
| 3,5-Bis-[2-(N,N—dimethylamino)ethyl] 2,6-dimethyl-4-(2'-pyridyl)-1,4-dihydropyridine-3,5-dicarboxylate | D-16 | —$CO_2CH_2CH_2NMe_2$ | 2-pyridyl | 205–207° |
| 3,5-Diethyl 2,6-dimethyl-4-(3'-pyridyl)-1,4-dihydropyridine-3,5-dicarboxylate | D-17 | —$CO_2Et$ | 3-pyridyl | 189–191° |
| 3,5-Diisopropyl 2,6-dimethyl-4-(g'-pyridyl-1,4-dihydropyridine-3-5-dicarboxylate | D-18 | —$CO_2$—i-Pr | 3-pyridyl | 213–215° |
| 3,5-Diisobutyl 2,6-dimethyl-4-(3'-pyridyl)-1,4-dihydropyridine-3,5-dicarboxylate | D-19 | —$CO_2$—i-Bu | 3-pyridyl | 169–171° |
| 3,5-Bis-[2-(N,N—dimethylamino)ethyl] 2,6-dimethyl-4-(3'pyridyl)-1,4-dihydropyridine-3,5-dicarboxylate | D-20 | —$CO_2CH_2CH_2NMe_2$ | 3-pyridyl | 152–153° |
| 3,5-Diethyl 2,6-dimethyl-4-(4'-pyridyl)-1,4-dihydropyridine-3,5-dicarboxylate | D-21 | —$CO_2Et$ | 4-pyridyl | 183–186° |
| 3,5-Diisopropyl 2,6-dimethyl-4-(4'-pyridyl)-1,4-dihydropyridine-3,5-dicarboxylate | D-22 | —$CO_2$—i-Pr | 4-pyridyl | 224–226° |
| 3,5-Diisobutyl 2,6-dimethyl-4-(4'-pyridyl)-1,4-dihydropyridine-3,5-dicarboxylate | D-23 | —$CO_2$—i-Bu | 4-pyridyl | 167–169° |
| 3,6-Bis-[2-(N,N—dimethylamino)ethyl] 2,6-dimethyl-4-(4'-pyridyl)-1,4-dihydropryidine-3,5-dicarboxylate | D-24 | —$CO_2CH_2CH_2NMe_2$ | 4-pyridyl | 161–163° |

Example 5

Methyl 3-cyano-2,6-dimethyl-4-(3'-pyridyl)-1,4-dihydropyridine-5-carboxylate (D-25)

(See schematic representation following example)

3-Aminocrotonitrile (8.2 g, 0.1 mol) was added to a solution of 3-pyridinecarboxaldehyde (10.7 g, 0.1 mol) and methyl-3-aminocrotonate (8.9 g, 0.1 mol) in ethanol (50 mL) with stirring and the reaction mixture was heated at reflux for 24 h. The reaction mixture was poured onto crushed ice (1000 mL) and the solid product that separated was filtered. Purification was effected by elution from a silica gel column using acetone-hexane (2:3 v/v) as eluant to afford the product as a white solid (73%) with mp 242°14 244° C.; IR ($CHCl_3$) 3192 (NH), 2220 (CN) and 1656 ($CO_2$) cm$^{-1}$; NMR (DMSO-$d_6$) 2.2 (s, 6H, =$CHCH_3$), 3.5 (s, 3H, $CO_2CH_3$), 4.7 (s, 1H, H-4), 7.45–8.0 (m, 2H, H-4', H-5'), 8.5–8.86 (m, 2H, H-2', H-6'), 9.8 (s, 1H, NH, exchanges with deuterium oxide). Anal. found: C, 66.78; H, 5.36; N, 15.25. $C_{15}H_{15}N_3O_2$ requires: C, 66.91; H, 5.58: N, 15.61.

Schematic for Example 5

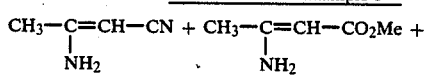

-continued
Schematic for Example 5

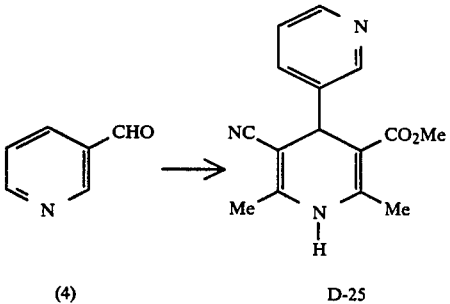

(4)    D-25

The positional isomer, methyl 3-cyano-4-(4'-pyridyl)-1,4-dihydropyridine-5-carboxylate (D-26) was prepared using a similar method, mp 195°–197°.

Example 6

3,5-dicyano-2,6-dimethyl-4-(3'-pyridyl)-1,4-dihydropyridine (D-27)

A solution of 3-pyridinecarboxaldehyde (10.7 g, 0.1 mol) and 3-aminocrotononitrile (17.8 g, 0.2 mol) in ethanol (50 mL) was heated under reflux for 24 h. The reaction mixture was poured onto crushed ice (100 mL) and the solid that separated was filtered. The product was purified by elution from a silica gel column using acetone-hexane (2:3 v/v) as eluant to afford the title compound as a white solid (63%) with mp 229°–230° C.; IR ($CHCl_3$) 3192 (NH) and 2220 (CN) cm$^{-1}$; NMR (DMSO-$d_6$) 2.1 (s, 6H, $CH_3$), 4.5 (s, 1H, H-4), 7.36–7.93 (m, 2H, H-4', H-5'), 8.5–8.7 (m, 2H, H-2', H-6'), 9.5 (s, 1H, NH, exchanges with deuterium oxide). Analysis found: C, 71.45; H, 5.32; N, 23.56. $C_{14}H_{12}N_4$ requires: C, 71.19; H, 5.08; N, 23.73.

The positional isomer, 3,5-dicyano-2,6-dimethyl-4-(4'-pyridyl)-1,4-dihydropyridine (D-28) was prepared using a similar reaction, mp 234–236.

Example 7

Methyl 2,6-dimethyl-3-nitro-4-(2'-pyridyl)-1,4-dihydropyridine-5-carboxylate (D-29)

1-Nitro-2-propanone (10.3 g, 0.1 mol) was added to a solution of 2-pyridinecarboxaldehyde (10.7 g, 0.1 mol) and methyl-3-aminocrotonate (8.9 g, 0.1 mol) in ethanol (100 mL) with stirring. The reaction mixture was heated under reflux for 24 h and was poured onto crushed ice (100 mL). Extraction with ethyl acetate (3×50 mL), drying the combind organic extracts ($MgSO_4$) and removal of the solvent in vacuo gave an oily residue which was dissolved in acetonitrile. Addition of ether precipitated the crude product which was purified by elution from a silica gel column using hexane-ethyl acetate-acetonitrile (1:1.5:2.5 v/v/v) as eluant to give the title compound (15.2%) with mp 192°–194° C.; IR ($CHCl_3$) 3160 (NH), 1710 ($CO_2$) and 1512 ($NO_2$) $cm^{-1}$; NMR (DMSO-$d_6$) 2.03 (s, 3H, C6—$CH_3$), 2.4 (s, 3H, C2—$CH_3$), 3.55 (s, 3H, $CO_2CH_3$), 4.6 (s, 1H, H-4), 7.36 (m, 2H, H-3', H-5'), 7.83 (d, J=8 Hz of d, J=8 Hz of d, J=2.5 Hz, 1H, H-4'), 8.7 (d, J=6 Hz of d, J=2 Hz, 1H, H-6'), 9.1 (s, 1H, NH, exchanges with deuterium oxide). Analysis found: C, 58.43; H, 5.26; N, 14.84. $C_{14}H_{15}N_3O_4$ requires: C, 58.13; H, 5.19; N, 14.53.

The positional isomers methyl 2,6-dimethyl-3-nitro-4-(3'-pyridyl)-1,4-dihydropyridine-5-carboxylate (D-30) with mp 199°–201° and methyl 2,6-dimethyl-3-nitro-4-(4'-pyridyl)-1,4-dihydropyridine-5-carboxylate (D-31) with mp 208°–210° were prepared using similar reactions.

Example 8

Dimethyl 2,6-dimethyl-4-{3'-[N-methoxycarbonyl-1',2'-dihydropyridyl]}-1,4-dihydropyridine-3,5-dicarboxylate (D-32a) and dimethyl 2,6-dimethyl-4-{3'-[N-methoxycarbonyl-1',6'-dihydropyridyl]}-1,4-dihydropyridine-3,5-dicarboxylate (D-32b).

(See schematic representation following the example)

Sodium borohydride (1.9 g, 0.05 mol) was added to a solution of dimethyl 2,6-dimethyl-4-(3'-pyridyl)-1,4-dihydropyridine-3,5-dicarboxylate (0.01 mol) in methanol (40 mL) precooled to −65° C. After 10 min, a solution of methyl chloroformate (0.015 mol) in dry ether (10 mL) was added dropwise with stirring. The reaction was allowed to proceed for 4 h at −65° C. with stirring. The mixture was poured onto crushed ice (50 mL) and was allowed to come to room temperature. The crude product was extracted using dichloromethane, the organic extracts were dried ($MgSO_4$) and the solvent removed in vacuo. The product which consisted of a mixture of the isomeric 1',2'- and 1',6'-dihydropyridyl products was purified by flash chromatography using hexane-ethyl acetate (1:1 v/v) as eluant, the two isomers (ratio 1',2':1'6'=9:7) as determined from $^1H$ nmr integrals could not be separated. Yield (73%); IR ($CHCl_3$) 3340 (NH) and 1680–1710 ($CO_2Me$, $NCO_2Me$) $cm^{-1}$; Isomer D-32A NMR (DMSO-$d_6$) 2.3 (s, 6H, =$CCH_3$), 3.63 (s, 6H, $CO_2CH_3$), 3.7 (s, 3H, $NCO_2CH_3$), 4.16 (s, 2H, H-2'), 4.36 (s, 1H, H-4), 5.22 (m, 1H, H-5'), 5.5 (d, J=5.5 Hz, 1H, H-4'), 6.56 (d, J=6.1 Hz, 1H, H-6'); 8.89 (s, 1H, NH, exchanges with deuterium oxide); Isomer D-32b NMR (DMSO-$d_6$) 2.3 (s, 6H, =$CCH_3$), 3.63 (s, 6H, $CO_2CH_3$), 3.7 (s, 3H, $NCO_2CH_3$), 4.2 (s, 2H, H-6'), 4.36 (s, 1H, H-4), 5.58 (m, $J_{4',5'}$=10.3 Hz, 1H, H-5'), 5.8 (d, $J_{4',5'}$=10.3 Hz, 1H, H-4'), 6.36 (s, 1H, H-2'), 8.98 (s, 1H, NH, exchanges with deuterium oxide). Analysis found: C, 59.59; H, 6.26; N, 7.26. $C_{18}H_{22}N_2O_6$ requires: C, 59.67; H, 6.07; N, 7.23.

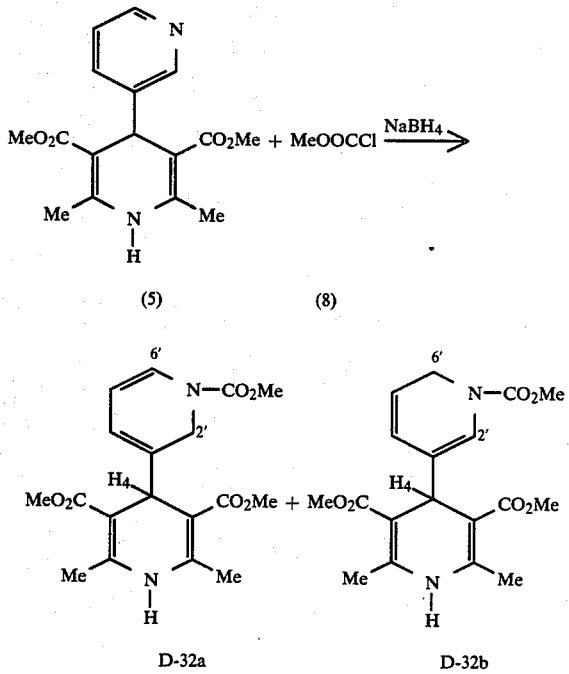

Schematic for Example 8

Related 3,5-disubstituted 2,6-dimethyl-4-{3'-[N-alkoxycarbonyl-1',2'-(1',6'-)dihydropyridyl]}-1,4-dihydropyridine derivatives have been prepared as shown in the schematic representation shown below using equivalent quantities of other 1,4-dihydropyridines of formula (5) and chloroformates of formula (8) using a procedure similar to that outlined in Example 8.

The melting point for each product is set out in Table 3.

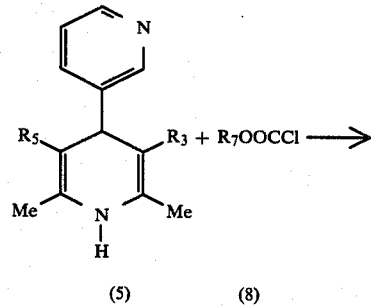

Schematic for Example 9

-continued
Schematic for Example 9

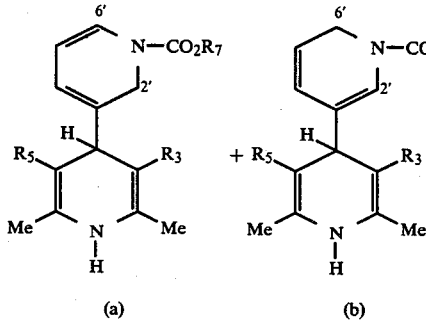

(a)     (b)

Example 10

Dimethyl 2,6-dimethyl-4-[4'-(N-methoxycarbonyl-1',2'-dihydropyridyl)]-1,4-dihydropyridine-3,5-dicarboxylate (D-51)

(See schematic representation following the example)

Sodium borohydride (1.9 g, 0.05 mol) was added to a solution of dimethyl 2,6-dimethyl-4-(4'-pyridyl)-1,4-dihydropyridine-3,5-dicarboxylate (0.01 mol) in methanol (40 mL) precooled to −65° C. After 10 min, a solution of methyl chloroformate (0.015 mol) in dry ether (10 mL) was added dropwise with stirring and the reaction was allowed to proceed for 6 h at −65° C. with stirring. The reaction mixture was poured onto crushed ice (50 mL) and allowed to return to 25° C. The crude product was extracted using dichloromethane, the organic extracts were dried ($MgSO_4$) and the solvent removed in vacuo. The solid residue obtained was purified by flash chromatography using hexane-ethyl acetate as eluant to give the title compound (73%); mp 182°–184° C.; IR ($CHCl_3$) 3310 (NH) and 1710 ($CO_2Me$, $NCO_2Me$) $cm^{-1}$; NMR (DMSO-$d_6$) 2.24 (s, 6H, =$CCH_3$), 3.6 (s, 6H, $CO_2CH_3$), 3.66 (s, 3H, $NCO_2CH_3$), 4.18 (broad s, 2H, H-2'), 4.38 (s, 1H, H-4), 5.05 (m, 1H, H-3'), 5.12 (m, 1H, H-5'), 6.62 (d, J=7 Hz, 1H, H-6'), 8.92 (s, 1H, NH, exchanges with deuterium oxide). Analysis found: C, 59.24; H, 6.26; N, 7.58. $C_{18}H_{22}N_2O_6$ requires: C, 59.67; H, 6.07; N, 7.73.

Schematic for Example 10

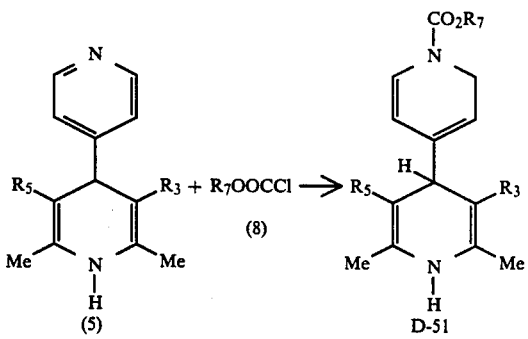

(5)     (8)     D-51

TABLE 3

3,5-Disubstituted 2,6-dimethyl-4-{3'-[N—alkoxycarbonyl-1',2'-(1',6')dihydropyridyl]}-1,4-dihydropyridine derivatives prepared according to Example 9

| Chemical Name | Designation | Ratio a:b | $R_3$ | $R_5$ | $R_7$ | mp |
|---|---|---|---|---|---|---|
| Diethyl 2,6-dimethyl-4-{3'-[N—methoxycarbonyl-1',2'-(1',6'-)dihydropyridyl]}-1,4-dihydropyridine-3,5-dicarboxylate | D-33 | 2:1 | —$CO_2Et$ | —$CO_3Et$ | Me | 115–116° |
| Diisopropyl 2,6-dimethyl-4-{3'-[N—methoxycarbonyl-1',2'-(1',6'-)dihydropyridyl]}-1,4-dihydropyridine-3,5-dicarboxylate | D-34 | 7:3 | —$CO_2$—i-Pr | —$CO_2$—i-Pr | Me | 151–153° |
| Diisobutyl 2,6-dimethyl-4-{3'-[N—methoxycarbonyl-1',2'(1',6'-)dihydropyridyl]}-1,4-dihydropyridine-3,5-dicarboxylate | D-35 | 5:3 | —$CO_2$—i-Bu | —$CO_2$—i-Bu | Me | 138–139° |
| Dimethyl 2,6-dimethyl-4-{3'-[N—phenoxycarbonyl-1',2'-(1',6'-)dihydropyridyl]}-1,4-dihydropyridine-3,5-dicarboxylate | D-36 | 3:1 | —$CO_2Me$ | —$CO_2Me$ | Ph | 147–149° |
| Diethyl 2,6-dimethyl-4-{3'-[N—phenoxycarbonyl-1',2'-(1',6'-)dihydropyridyl]}-1,4-dihydropyridine-3,5-dicarboxylate | D-37 | 4:3 | —$CO_2Et$ | —$CO_2Me$ | Ph | 162–164° |
| Diisopropyl 2,6-dimethyl-4-{3'-[N—phenoxycarbonyl-1',2'-(1',6'-)dihydropyridyl]}-1,4-dihydropyridine-3,5-dicarboxylate | D-38 | 4:3 | —$CO_2$—i-Pr | —$CO_2$—i-Pr | Ph | 114–116° |
| Diisobutyl 2,6-dimethyl-4-{3'-[N—phenoxycarbonyl-1',2'-(1',6'-)dihydropyridyl]}-1,4-dihydropyridine-3,5-dicarboxylate | D-39 | 2:1 | —$CO_2$—i-Bu | —$CO_2$—i-Bu | Ph | 172–174° |
| Diethyl 2,6-dimethyl-4-{3'-[N—t-butoxycarbonyl-1',2'-(1',6'-)dihydropyridyl]}-1,4-dihydropyridine-3,5-dicarboxylate | D-40 | 2:1 | —$CO_2Et$ | —$CO_2Et$ | t-Bu | 152–154° |
| Diisopropyl 2,6-dimethyl-4-{3'-[N—t-butoxycarbonyl-1',2'-(1',6'-)dihydropyridyl]}-1,4-dihydropyridine-3,5-dicarboxylate | D-41 | 7:3 | —$CO_2$—i-Pr | —$CO_2$—i-Pr | t-Bu | 148–150° |
| Diisobutyl 2,6-dimethyl-4-{3'-[N—t-butoxycarbonyl-1',2'-(1',6'-)dihydropyridyl]}-1,4-dihydropyridine-3,5-dicarboxylate | D-42 | 2:1 | —$CO_2$—i-Bu | —$CO_2$—i-Bu | t-Bu | 153–155° |
| 3-Isobutyl-5-methyl 2,6-dimethyl-4-{3'-[N—methoxycarbonyl-1',2'-(1',6'-)dihydropyridyl]}-1,4-dihydropyridine-3,5-dicarboxylate | D-43 | 3:1 | —$CO_2$—i-Bu | —$CO_2Me$ | Me | 181–183° |
| 3-Isobutyl-5-methyl 2,6-dimethyl-4-{3'-[N—phenoxycarbonyl-1',2'-(1',6'-)dihydropyridyl]}-1,4-dihydropyridine-3,5-dicarboxylate | D-44 | 10:3 | —$CO_2$—i-Bu | —$CO_2Me$ | Ph | 162–163° |
| 3-Isopropyl-5-methyl 2,6-dimethyl-4-{3'-[N—t-butoxycarbonyl-1',2'-(1',6'-)dihydropyridyl]}-1,4-dihydropyridine-3,5-dicarboxylate | D-45 | 4:1 | —$CO_2$—i-Pr | —$CO_2Me$ | t-Bu | 136–138° |
| 3-Methyl 5-cyano-2,6-dimethyl-4-{3'-[N—methoxycarbonyl-1',2'-(1',6'-)dihydropyridyl]}-1,4-dihydropyridine-3-carboxylate | D-46 | 5:3 | —$CO_2Me$ | CN | Me | 125–127° |
| 3-Methyl 5-cyano-2,6-dimethyl-4-{3'-[N—phenoxycarbonyl-1',2'-(1',6'-)dihydropyridyl]}-1,4-dihydropyridine-3-carboxylate | D-47 | 11:9 | —$CO_2Me$ | CN | Ph | 131–132° |
| 3,5-Dicyano-2,6-dimethyl-4-{3'-[N—methoxycarbonyl-1',2'-(1',6'-)dihydropyridyl]}-1,4-dihydropyridine | D-48 | 5:3 | CN | CN | Me | 136–138° |
| 3,5-Dicyano-2,6-dimethyl-4-{3'-[N—phenoxycarbonyl-1',2'-(1',6'-)dihydropyridyl]}-1,4-dihydropyridine | D-49 | 7:3 | CN | CN | Ph | 151–153° |
| 3,5-Dicyano-2,6-dimethyl-4-{3'-[N—t-butoxycarbonyl-1',2'-(1',6'-)dihydropyridyl]}-1,4-dihydropyridine | D-50 | 2:1 | CN | CN | t-Bu | 145–147° |

Example 11

Related 3,5-disubstituted 2,6-dimethyl-4-{4'-[N-alkoxycarbonyl-1',2'-dihydropyridyl]}-1,4-dihydropyridine derivatives have been prepared as shown in the schematic representation shown below using equivalent quantities of other 1,4-dihydropyridines of formula (5) and chloroformates of formula (8) using a procedure similar to that outlined in Example 10.

The melting point of each product is set out in Table 4.

Schematic for Example 11

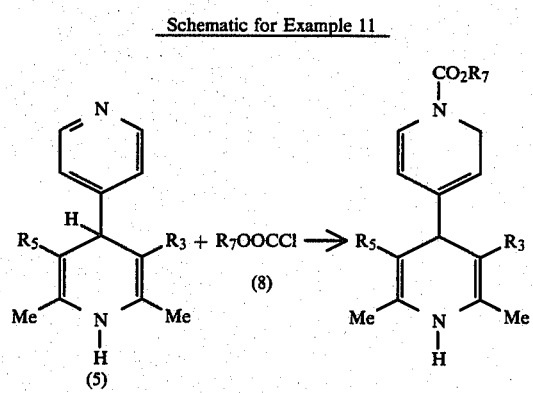

Example 12

Dimethyl 2,6-dimethyl-4-[2'-(N-methyl-1',2',3',6'-tetrahydropyridyl-]-1,4-dihydropyridine-3,5-dicarboxylate (D-64)

(See schematic representation following the example)

A solution of dimethyl 2,6-dimethyl-4-(2'-pyridyl)-1,4-dihydropyridine-3,5-dicarboxylate (0.1 mol) in acetone (50 mL) was added to iodomethane (4.25 g, 0.03 mol) and the mixture was heated under reflux for 9 h. The reaction mixture was cooled to 25° C. and the solvent was removed in vacuo. The pyridinium iodide was dissolved in 20 mL ethanol-water (1:1 v/v) and cooled to 0° C. This solution was then added to a solution of sodium borohydride (1.9 g, 0.05 mol) in absolute ethanol (15 mL) precooled to 0° C. The reduction was allowed to proceed for 5 h at 0° C. Water (50 mL) was added and the solid product was isolated by filtration. Recrystallization from aqueous ethanol (1:1 v/v, 10 mL) gave the title compound (78%); mp 159°–161° C.; IR (CHCl$_3$) 1630 (C=C), 1670 (CO$_2$) and 1280 (C-N) cm$^{-1}$; NMR (CDCl$_3$) 1.7–1.9 and 1.9–2.06 (two m, 1H each, H-3'), 2.33 (s, 6H, =CCH$_3$), 2.37 (s, 3H, NCH$_3$), 2.3–2.46 (m, 1H, H-2'), 3.12 (m, 2H, H-6'), 3.75 and 3.77 (two s, 3H each, CO$_2$CH$_3$), 4.3 (d, J=7.72 Hz, 1H, H-4), 5.5–5.64 (m, 1H, H-5'), 5.64–5.8 (m, $J_{4',5'}$=10 Hz, 1H, H-4'), 6.38 (s, 1H, NH, exchanges with deuterium oxide). Analysis found: C, 63.42; H, 7.36; N, 9.06. C$_{17}$H$_{24}$N$_2$O$_4$ requires: C, 63.75; H, 7.50;, N, 8.75.

Schematic for Example 12

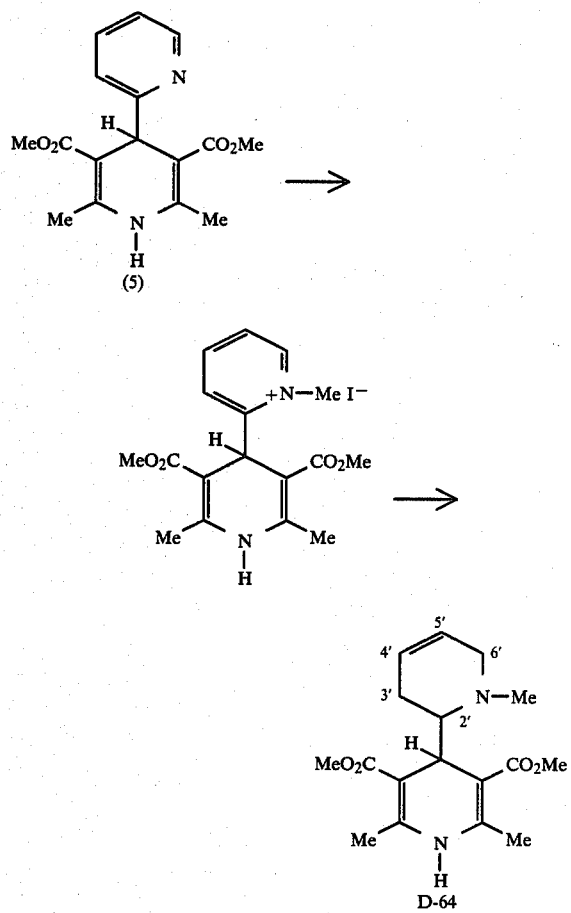

Related dialkyl 2,6-dimethyl-4-{2'-(4',5')[N-methyl-1',2',3',6'-tetrahydropyridyl]}-1,4-dihydropyridine-3,5-dicarboxylate derivatives have been prepared as shown in the schematic representation shown below using equivalent quantities of othr dialkyl 2,6-dimethyl-4-[2'-(3'-4'-)pyridyl]-1,4-dihydropyridine-3,5-dicarboxylates of formula (5) and methyl iodide of formula (11) using a similar procedure to that outlined in Example 12.

The melting point of each product is set out in Table 5.

TABLE 4

3,5-Disubstituted 2,6-dimethyl-4-[4'-N—alkoxycarbonyl]-1,4-dihydropyridine derivatives prepared according to Example 11

| Chemical Name | Designation | R$_3$ | R$_5$ | R$_7$ | mp |
|---|---|---|---|---|---|
| Diethyl 2,6-dimethyl-4-[4'-(N—methoxycarbonyl)]-1,4-dihydropyridine-3,5-dicarboxylate | D-52 | —CO$_2$Et | —CO$_2$Et | Me | 145–148° |
| Diisobutyl 2,6-dimethyl-4-[4'-(N—methoxycarbonyl)]-1,4-dihydropyridine-3,5-dicarboxylate | D-53 | —CO$_2$—i-Bu | —CO$_2$—i-Bu | Me | 161–163° |
| Dimethyl 2,6-dimethyl-4-[4'-(N—phenoxycarbonyl)]-1,4-dihydropyridine-3,5-dicarboxylate | D-54 | —CO$_2$Me | —CO$_2$Me | Ph | 159–161° |
| Diethyl 2,6-dimethyl-4-[4'-(N—phenoxycarbonyl)]-1,4-dihydropyridine-3,5-dicarboxylate | D-55 | —CO$_2$Et | —CO$_2$Et | Ph | 128–129° |
| Diisobutyl 2,6-dimethyl-4-[4'-(N—phenoxycarbonyl)]-1,4-dihydropyridine-3,5-dicarboxylate | D-56 | —CO$_2$—i-Bu | —CO$_2$—i-Bu | Ph | 167–169° |
| Diethyl 2,6-dimethyl-4-[4'-(N—t-butoxycarbonyl)]-1,4-dihydropyridine-3,5-dicarboxylate | D-57 | —CO$_2$Et | —CN | t-Bu | 165–167° |
| Diisobutyl 2,6-dimethyl-4-[4'-(N—t-butoxycarbonyl)]-1,4-di- | D-58 | —CO$_2$—i-Bu | —CO$_2$—i-Bu | Me | 126–128° |

TABLE 4-continued 3,5-Disubstituted 2,6-dimethyl-4-[4'-N—alkoxycarbonyl]-1,4-dihydropyridine derivatives prepared according to Example 11

| Chemical Name | Designation | $R_3$ | $R_5$ | $R_7$ | mp |
|---|---|---|---|---|---|
| hydropyridine-3,5-dicarboxylate | | | | | |
| 3,5-Dicyano-2,6-dimethyl-4-[4'-(N—methoxycarbonyl)]-1,4-dihydropyridine | D-59 | CN | —CN | Me | 157–159° |
| 3-Isobutyl-5-methyl 2,6-dimethyl-4-[4'-(N—methoxycarbonyl)]--1,4-dihydropyridine-3,5-dicarboxylate | D-60 | —$CO_2$—i-Bu | —$CO_2$Me | Me | 171–173° |
| 3-Isobutyl-5-methyl 2,6-dimethyl-4-[4'-(N—phenoxycarbonyl)]-1,4-dihydropyridine-3,5-dicarboxylate | D-61 | —$CO_2$—i-Bu | —$CO_2$Me | Ph | 168–169° |
| 3-Isopropyl-5-methyl 2,6-dimethyl-4-[4'-(N—t-butoxycarbonyl)]-1,4-dihydropyridine-3,5-dicarboxylate | D-62 | —$CO_2$—i-Pr | —$CO_2$Me | t-Bu | 173–175° |
| 3-Isobutyl-5-methyl 2,6-dimethyl-4-[4'-(N—t-butoxycarbonyl)]-1,4-dihydropyridine-3,5-dicarboxylate | D-63 | —$CO_2$—i-Bu | —$CO_2$Me | t-Bu | 148–149° |

TABLE 5

Dialkyl 2,6-dimethyl-4-{2'-(4'-,5'-)[N—methyl-1',2',3',6'-tetrahydropyridyl]}-1,4-dihydropyridine-3,5-dicarboxylates prepared according to Example 13

| Chemical Name | Designation | $R_3$ | $R_5$ | $R_4$ | mp |
|---|---|---|---|---|---|
| Diethyl 2,6-dimethyl-4-[2'-(N—methyl-1',2',3',6'-tetrahydropyridyl)]-1,4-dihydropyridine-3,5-dicarboxylate | D-65 | —$CO_2$Et | —$CO_2$Et | 2'-thp | 131–133° |
| Dimethyl 2,6-dimethyl-4-[4'-(N—methyl-1',2',3',6'-tetrahydropyridyl)]-1,4-dihydropyridine-3,5-dicarboxylate | D-66 | —$CO_2$Me | —$CO_2$Me | 4'-thp | 133–134° |
| Diethyl 2,6-dimethyl-4-[4'-(N—methyl-1',2',3',6'-tetrahydropyridyl)]-1,4-dihydropyridine-3,5-dicarboxylate | D-67 | —$CO_2$Et | —$CO_2$Et | 4'-thp | 114–116° |
| Dimethyl 2,6-dimethyl-4-[5'-(N—methyl-1',2',3',6'-tetrahydropyridyl)]-1,4-dihydropyridine-3,5-dicarboxylate | D-68 | —$CO_2$Me | —$CO_2$Me | 5'-thp | 161–162° |
| Diethyl 2,6-dimethyl-4-[5'-(N—methyl-1',2',3',6'-tetrahydropyridyl)]-1,4-dihydropyridine-3,5-dicarboxylate | D-69 | —$CO_2$Et | —$CO_2$Et | 5'-thp | 125–126° |

Schematic for Example 13

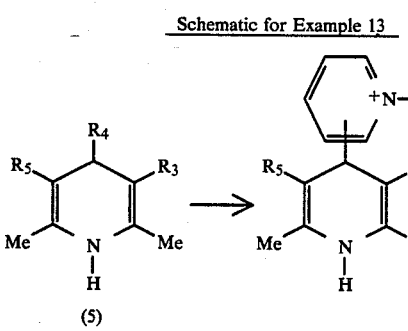

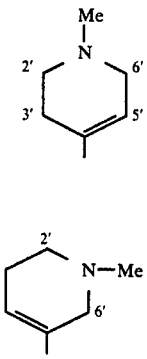

5'-thp; 5'-(N—methyl-1',2',3',6'-tetrahydropyridyl), $R_4$ substituents:

2'-thp; 2'-(N—methyl-1',2',3',6'-tetrahydropyridyl),

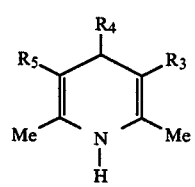

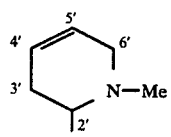

4'-thp; 4'-(N—methyl-1',2',3',6'-tetrahydropyridyl),

Example 14

Dimethyl 1,2,6-trimethyl-4-(4-trifluoromethylphenyl)-1,2-dihydropyridine-3,5-dicarboxylate (W-1)

(See schematic representation following the example)

A solution of ammonium hydroxide (30% w/v, 5 mL) was added to a solution of 4-trifluoromethylbenzaldehyde I (52 mmol) and methyl acetoacetate II (12 g, 103 mmol) in 98% ethanol (25 mL) with stirring and the mixture was heated at reflux for 30 h. The reaction mixture was cooled and poured onto 500 mL ice water. The sticky solid which precipitated was removed by filtration, washed with ether and recrystallized from water-ethanol (1:4 v/v) to give III (13 g, 69%), mp 187°–188° C.

Sodium nitrate (1.6 g, 18.7 mmol) was added to a warm solution of III (5 mmol) in glacial acetic acid (15 mL) with vigorous stirring. The mixture was heated at 100° C. for 4 h, cooled to 25° C. and poured onto ice water (150 ml). The resulting precipitate was filtered and recrystallized from ether-petroleum ether (1:9 v/v) to give IV (0.88 g, 48%), mp 77°–79°.

Dimethyl sulfate (1.3 mL, 13.8 mmol) and IV (2.7 mmol) were placed in a pressure flask which was heated at 70° C. in an oil bath for 70 h. The resulting dark brown oil was washed several times with ether, dissolved in water (30 mL) and the aqueous solution was washed with water. The aqueous layer was separated and the solvent removed in vacuo to give V as an oil. The oil V was dissolved in a minimum quantity of water and filtered. A saturated solution of aqueous sodium perchlorate was then added slowly until there was no further formation of white precipitate. The precipitate was filtered, washed several times with water and recrystallized from water-methanol (3:7 v/v) to give VI (0.97 g, 74%), mp 173° C.

Sodium carbonate (1.07 g, 10 mmol) was added to a solution of VI (1.98 mmol) in 98% ethanol (70 ml) and distilled water (7 mL) and the mixture was stirred at 0° C. for 1 h. Sodium borohydride (0.107 g, 2.8 mmol) was added and the reaction mixture was stirred at 25° C. for 20 min. The reaction mixture was filtered and the solvents removed in vacuo. The residue obtained was extracted with diethyl ether, dried ($Na_2SO_4$), filtered, the solvent removed in vacuo and the product recrystallized from petroleum ether to give dimethyl 1,2,6-trimethyl-4-(4-trifluoromethylphenyl)-1,2-dihydropyridine-3,5-dicarboxylate W-1 (0.68 g, 90%); mp 94°–95° C.; IR (KBr) 1687 ($CO_2Me$) and 1615 (C=C) cm$^{-1}$; NMR ($CDCl_3$) 1.22 (d, J=6 Hz, 3H, CH—$\underline{CH_3}$), 2.45 (s, 3H, =$\underline{CCH_3}$), 3.06 (s, 3H, $NCH_3$), 3.26 and 3.42 (two 2, 3H each, $CO_2CH_3$), 4.6 (q, J=6 Hz, 1H, $\underline{CH}$—$CH_3$), 7.3 and 7.65 (two d, J32 9 Hz, 2H each, phenyl hydrogens); Mass Spectrum; m/z 383.25 (M$^+$). Analysis found: C, 59.63; H, 5.20; N, 3.57. $C_{19}H_{20}F_3NO_4$ requires: C, 59.53; H, 5.26; N, 3.65.

Schematic for Example 14

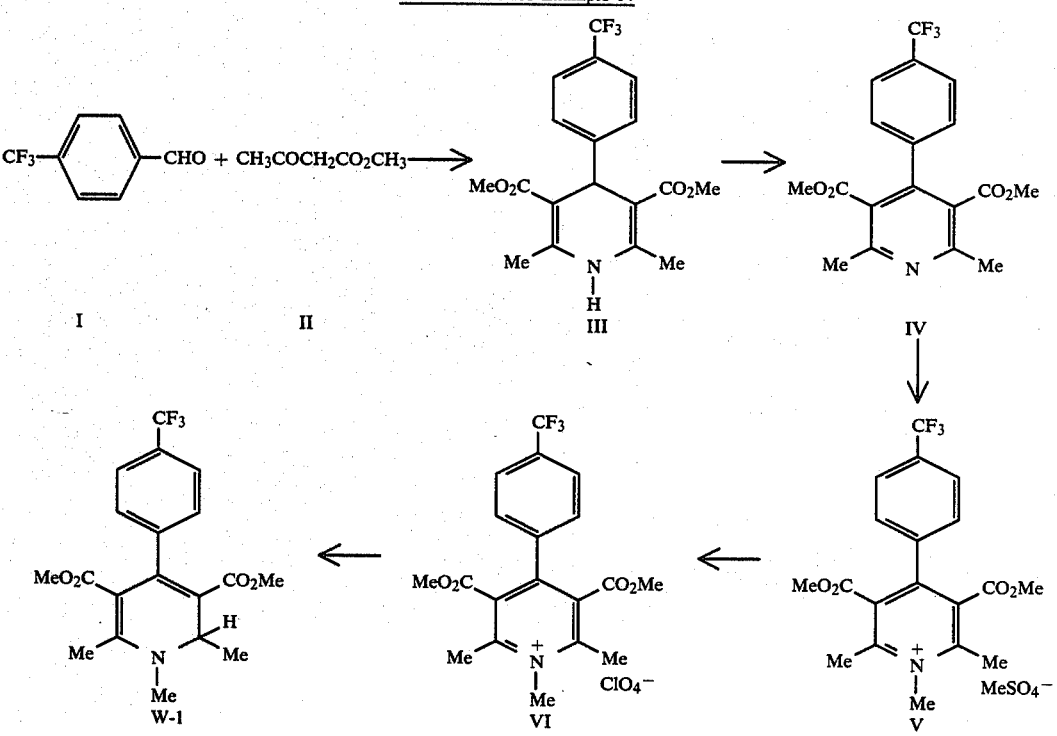

Example 15

Related dialkyl 1,2,6-trimethyl-4-(substituted phenyl)-1,2-dihydropyridine-3,5-dicarboxylate derivatives have been prepared as shown in the schematic representation shown below using equivalent quantities of other aldehydes of formula (14) and acetoacetates of formula (15) using a similar reaction procedure to that outlined in Example 14.

The melting point of each product is set out in Table 6.

Schematic for Example 15

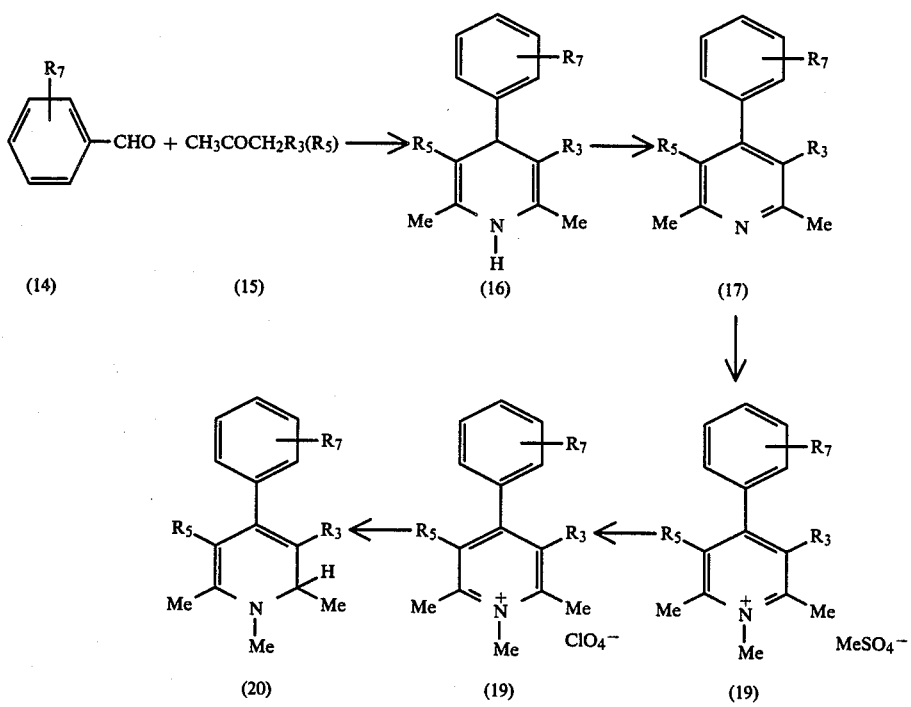

TABLE 6

Dialkyl 1,2,6-trimethyl-4-(substituted phenyl)-1,2-dihydropyridine-3,5-dicarboxylate derivatives prepared according to Example 15

| Chemical Name | Designation | $R_3$ | $R_5$ | $R_7$ | mp |
|---|---|---|---|---|---|
| Dimethyl 1,2,6-trimethyl-4-phenyl-1,2-dihydropyridine-3,5-dicarboxylate | S-1 | $-CO_2Me$ | $-CO_2Me$ | H | 117° |
| Dimethyl 1,2,6-trimethyl-4-(3-trifluoromethylphenyl)-1,2-dihydropyridine-3,5-dicarboxylate | S-2 | $-CO_2Me$ | $-CO_2Me$ | 3-$CF_3$ | oil |
| Dimethyl 1,2,6-trimethyl-4-(2-trifluoromethylphenyl)-1,2-dihydropyridine-3,5-dicarboxylate | S-3 | $-CO_2Me$ | $-CO_2Me$ | 2-$CF_3$ | 108° |
| Dimethyl 1,2,6-trimethyl-4-(4-nitrophenyl)-1,2-dihydropyridine-3,5-dicarboxylate | S-4 | $-CO_2Me$ | $-CO_2Me$ | 4-$NO_2$ | 114° |
| Dimethyl 1,2,6-trimethyl-4-(3-nitrophenyl)-1,2-dihydropyridine-3,5-dicarboxylate | S-5 | $-CO_2Me$ | $-CO_2Me$ | 3-$NO_2$ | 49° |
| Dimethyl 1,2,6-trimethyl-4-(2-nitrophenyl)-1,2-dihydropyridine-3,5-dicarboxylate | S-6 | $-CO_2Me$ | $-CO_2Me$ | 2-$NO_2$ | 146° |
| 3-Methyl-5-isopropyl 1,2,6-trimethyl-4-(2-nitrophenyl)-1,2-dihydropyridine-3,5-dicarboxylate | W-2 | $-CO_2Me$ | $-CO_2-i-Pr$ | 2-$NO_2$ | oil |
| 3-Isopropyl-5-methyl 1,2,6-trimethyl-4-(2-nitrophenyl)-1,2-dihydropyridine-3,5-dicarboxylate | W-3 | $-CO_2-i-Pr$ | $-CO_2Me$ | 2-$NO_2$ | oil |
| Diisopropyl 1,2,6-trimethyl-4-(2-nitrophenyl)-1,2-dihydropyridine-3,5-dicarboxylate | W-4 | $-CO_2-i-Pr$ | $-CO_2-i-Pr$ | 2-$NO_2$ | 140° |

CALCIUM CHANNEL ANTAGONIST TESTING

Calcium channel antagonist activity was determined as the concentration required to produce 50% inhibition of the muscarinic receptor-mediated $Ca^{2+}$-dependent contraction of guinea pig ileal longitudinal smooth muscle assay (C. Triggle, V. Swamy and D. Triggle, Can. J. Physiol. Pharmacol., 1979, 57, 804). Male albino guinea pigs (body weight 300–450 g) were sacrificed by decapitation. The intestine was removed above the ileo-caecal junction. Longitudinal smooth muscle segments of 2 cm length were mounted under a resting tension of 300–400 mg. The segments were maintained at 37° C. in a 10 mL jacketed organ bath containing oxygenated (100% $O_2$) physiological saline solution of the following composition (mM): NaCl: 137; $CaCl_2$: 2.6; KCl: 5.9; $MgCl_2$: 1.2; glucose: 11.9; buffered by Hepes-NaOH to pH 7.4. The muscles were equilibrated for 1 h with a solution change every 15 min. Two successive control contractions were elicited at 15 min intervals with $5 \times 10^{-7}$M cis-2-methyl-4-dimethylaminomethyl-1,3-dioxolane methiodide (CD). The isometric contractions were recorded with a force displacement transducer (FT 03C) on a GRASS physiograph. The means of the two contractile responses was taken as the 100% value for the tonic (slow) component of the response. The muscle was washed with Hepes saline solution and was allowed to re-equilibrate. The calcium antagonist (test compound) was added ten min before the dose-response for CD was determined. The drug-induced inhibition of contraction was expressed as percent of control. The $ID_{50}$ values were graphically determined from the concentration-response curves. The test results are shown in Table 7, the compounds testing being compared to Nifedipine (TM).

TABLE 7

Calcium channel antagonist antihypertensive activity for 3,5-disubstituted 2,6-dimethyl-4-(pyridyl)-1,4-dihydropyridine, 3,5-disubstituted 2,6-dimethyl-4-{3'-[N—alkoxycarbonyl-1',2'-(1',6'-)dihydropyridyl]}-1,4-dihydropyridine, 3,5-disubstituted 2,6-dimethyl-4-{4'-[N—alkoxycarbonyl-1',2'-dihydropyridyl]}-1,4-dihydropyridine, dialkyl 2,6-dimethyl-4-{2'-(4'-,5'-)[N—methyl-1',2',3',6'-tetrahydropyridyl]}-1,4-dihydropyridine,-3,5-dicarboxylate and dialkyl1,2,6-trimethyl-4-(substituted phenyl)-1,2-dihydropyridine-3,5-dicarboxylate derivatives tested.

| Substance | Calcium channel antagonist act., inhib. act. on contractile response to CD[a] ID$_{50}$ (M)[b] |
|---|---|
| D-1 | $2.32 \pm 0.19 \times 10^{-6}$ (3)[c] |
| D-2 | $9.56 \pm 1.4 \times 10^{-8}$ (3)[c] |
| D-3 | $4.1 \pm 0.17 \times 10^{-8}$ (3)[c] |
| D-4 | $4.36 \pm 0.5 \times 10^{-5}$ (4)[c] |
| D-5 | $3.83 \pm 0.83 \times 10^{-6}$ (3)[c] |
| D-6 | $9.7 \pm 4.6 \times 10^{-8}$ (4)[c] |
| D-7 | $5.6 \pm 0.6 \times 10^{-5}$ (4)[c] |
| D-8 | $3.34 \pm 0.5 \times 10^{-5}$ (4)[c] |
| D-9 | $5.0 \pm 1.1 \times 10^{-6}$ (2) |
| D-10 | $5.6 \pm 1.6 \times 10^{-7}$ (3)[c] |
| D-11 | $2.2 \pm 0.7 \times 10^{-7}$ (3)[c] |
| D-12 | $5.13 \pm 0.4 \times 10^{-5}$ (4)[c] |
| D-13 | $1.8 \pm 0.03 \times 10^{-7}$ (3)[c] |
| D-14 | $1.25 \pm 0.2 \times 10^{-7}$ (3)[c] |
| D-15 | $9.36 \pm 1.4 \times 10^{-8}$ (4)[c] |
| D-17 | $3.46 \pm 1.2 \times 10^{-7}$ (3)[c] |
| D-18 | $2.6 \pm 0.6 \times 10^{-7}$ (3)[c] |
| D-19 | $1.46 \pm 0.6 \times 10^{-7}$ (3)[c] |
| D-20 | $1.79 \pm 0.2 \times 10^{-4}$ (4)[c] |
| D-22 | $2.31 \pm 0.67 \times 10^{-7}$ (4)[c] |
| D-23 | $5.8 \pm 2.1 \times 10^{-7}$ (3)[c] |
| D-26 | $8.77 \pm 0.4 \times 10^{-5}$ (3)[c] |
| D-27 | $3.57 \pm 0.72 \times 10^{-4}$ (3)[c] |
| D-28 | $1.3 \pm 0.2 \times 10^{-4}$ (2) |
| D-32 | $5.89 \pm 2.2 \times 10^{-7}$ (4)[c] |
| D-33 | $1.8 \pm 0.5 \times 10^{-7}$ (3)[c] |
| D-34 | $1.31 \pm 0.2 \times 10^{-7}$ (4)[c] |
| D-35 | $7.71 \pm 1.7 \times 10^{-7}$ (3)[c] |
| D-36 | $3.7 \pm 0.5 \times 10^{-6}$ (4)[c] |
| D-37 | $8.65 \pm 0.3 \times 10^{-7}$ (4)[c] |
| D-38 | $1.67 \pm 0.2 \times 10^{-6}$ (3)[c] |
| D-39 | $6.46 \pm 0.9 \times 10^{-6}$ (3)[c] |
| D-40 | $6.72 \pm 0.9 \times 10^{-7}$ (4)[c] |
| D-42 | $3.42 \pm 0.4 \times 10^{-6}$ (3)[c] |
| D-43 | $3.1 \pm 0.7 \times 10^{-8}$ (4)[c] |
| D-44 | $4.5 \pm 1.5 \times 10^{-8}$ (3)[c] |
| D-46 | $5.2 \pm 1.2 \times 10^{-5}$ (3)[c] |
| D-48 | $3.4 \pm 0.2 \times 10^{-5}$ (4)[c] |
| D-56 | $5.1 \pm 1.6 \times 10^{-7}$ (3)[c] |
| D-59 | $6.75 \pm 2.5 \times 10^{-5}$ (2) |
| D-60 | $1.76 \pm 0.5 \times 10^{-6}$ (4)[c] |
| D-61 | $8.1 \pm 3.5 \times 10^{-5}$ (3)[c] |
| D-64 | $6.47 \pm 0.24 \times 10^{-5}$ (3)[c] |
| D-65 | $1.3 \pm 0.05 \times 10^{-5}$ (3)[c] |
| D-66 | $1.81 \pm 0.5 \times 10^{-4}$ (3)[c] |
| D-67 | $4.96 \pm 1.33 \times 10^{-6}$ (3)[c] |
| D-68 | $3.43 \pm 0.5 \times 10^{-6}$ (3)[c] |
| D-69 | $1.1 \pm 0.7 \times 10^{-6}$ (3)[c] |
| S-1 | $2.15 \pm 0.5 \times 10^{-6}$ (2) |
| W-1 | $8.92 \pm 1.06 \times 10^{-6}$ (3)[c] |
| S-2 | $3.5 \pm 0.8 \times 10^{-6}$ (3)[c] |
| S-3 | $1.2 \pm 0.1 \times 10^{-5}$ (3)[c] |
| S-4 | $2.35 \pm 0.68 \times 10^{-5}$ (4)[c] |
| S-5 | $7.9 \pm 1.6 \times 10^{-6}$ (2) |
| S-6 | $2.52 \pm 0.23 \times 10^{-6}$ (4)[c] |
| W-2 | $2.0 \pm 0.14 \times 10^{-5}$ (7)[c] |
| W-3 | $1.05 \pm 0.11 \times 10^{-5}$ (7)[c] |
| W-4 | $5.73 \pm 0.3 \times 10^{-6}$ (7)[c] |
| Nifedipine (Tm) | $1.4 \pm 0.19 \times 10^{-8}$ (18)[c] |

Compounds D-2, D-3, D-6, D-7, D-10, D-11, D-14, D-15, D-17, D-18, D-19, D-22, D-23, D-32, D-33, D-34, D-35, D-37, D-40, D-43, D-44 and D-56 are active calcium channel antagonists, being comparable to Nifedipine (TM).

CALCIUM CHANNEL AGONIST TESTING
(D-30)

Methyl 2,6-dimethyl-3-nitro-4-(3'-pyridyl)-1,4-dihydropyridine-5-carboxylate (D-30) when tested using the calcium channel antagonist testing procedure caused muscle contraction. A modified protocol, used for testing calcium channel antagonists (vide supra), was used to determine the concentration at which D-30 produced 50% of the maximum contractile response. D-30 was administered in the place of CD and the dose-response curve was determined. A calcium antagonist was not added during the experiment. The effective dose of D-30 producing 50% of the maximum contractile response was $9.4 \times 10^{-5}$M. D-30 is therefore a calcium channel agonist which promotes calcium entry into cells as Bay K 8644 (M. Schramm, G. Thomas, R. Towart and G. Franckowiak, Nature, 1983, 303, 1983) and CGP 28392 (P. Erne, E. Burgisser, F. Buhler, B. Dubache, H. Kahnis, M. Mier and H. Robb, Biochem. Biophys. Res. Commun., 1984, 118, 842). Similarly, the effective dose of the isomeric D-31 producing 50% of the maximum contractile response was $6.6 \times 10^{-5}$M. Both D-30 and D-31 increased the guinea pig right atria heart rate by 30%.

We claim:

1. A dihydropyridine of the formula (1):

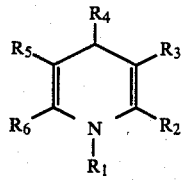

(1)

or a non-toxic pharmaceutically acceptable salt thereof, wherein $R_1$ is a hydrogen atom, lower alkyl group, lower alkyl carbonyl group or lower alkoxy carbonyl group; $R_2$ is a lower alkyl group; $R_3$ is a lower alkoxy carbonyl group, (N,N-dialkylamino) lower alkoxy carbonyl group, (N-lower alkyl-N-phenyl lower alkylamino) lower alkoxy carbonyl group, lower alkoxy lower alkoxy carbonyl group, nitro group or cyano group; $R_4$ is a member selected from the group consisting of a N-lower alkoxy carbonyl-1,2-dihydropyridyl group, N-lower alkyl carbonyl-1,2-dihydropyridyl group, N-phenoxy carbonyl-1,2-dihydropyridyl group, N-lower alkoxy carbonyl-1,6-dihydropyridyl group, N-lower alkyl carbonyl-1,6-dihydropyridyl group, N-phenoxy carbonyl 1,6-dihydropyridyl group, N-lower alkoxy carbonyl-1,4-dihydropyridyl group, N-lower alkyl carbonyl-1,4-dihydropyridyl group, N-phenoxy carbonyl 1,4-dihydropyridyl group, N-lower alkyl 1,2,3,6-tetrahydropyridyl group, N-lower alkoxycarbonyl-1,2,3,6-tetrahydropyridyl group, and N-lower alkyl carbonyl-1,2,3,6-tetrahydropyridyl group,; $R_5$ is a member selected from the group consisting of a lower alkoxy carbonyl group, (N,N-lower dialkylamino) lower alkoxy carbonyl group, (N-lower alkyl-N-phenyl lower alkyl amino) lower alkoxy carbonyl group, lower alkoxy lower alkoxy carbonyl group, nitro groyp and cyano group and $R_6$ is a lower alkyl group.

2. dimethyl 2,6-dimethyl-4-{3'-[N-methoxycarbonyl-1',2'-dihydropyridyl]}-1,4-dihydropyridine-3,5-dicarboxylate according to claim 1.

3. dimethyl 2,6-dimethyl-4-{3'-[N-methoxycarbonyl-1',6'-dihydropyridyl]}-1,4-dihydropyridine-3,5-dicarboxylate according to claim 1.

4. diethyl 2,6-dimethyl-4-{3'-[N-methoxycarbonyl-1',2'-dihydropyridyl]}-1,4-dihydropyridine-3,5-dicarboxylate according to claim 1.

5. diethyl 2,6-dimethyl-4-{3'-[N-methoxycarbonyl-1',6'-dihydropyridyl]}-1,4-dihydropyridine-3,5-dicarboxylate according to claim 1.

6. diisopropyl 2,6-dimethyl-4-{3'-[N-methoxycarbonyl-1',2'-dihydropyridyl]}-1,4-dihydropyridine-3,5-dicarboxylate according to claim 1.

7. diisopropyl 2,6-dimethyl-4-{3'-[N-methoxycarbonyl-1',6'-dihydropyridyl]}-1,4-dihydropyridine-3,5-dicarboxylate according to claim 1.

8. diisobutyl 2,6-dimethyl-4-{3'-[N-methoxycarbonyl-1',2'-dihydropyridyl]}-1,4-dihydropyridine-3,5-dicarboxylate according to claim 1.

9. diisobutyl 2,6-dimethyl-4-{3'-[N-methoxycarbonyl-1',6'-dihydropyridyl]}-1,4-dihydropyridine-3,5-dicarboxylate according to claim 1.

10. dimethyl 2,6-dimethyl-4-{3'-[N-phenoxycarbonyl-1',2'-dihydropyridyl]}-1,4-dihydropyridine-3,5-dicarboxylate according to claim 1.

11. dimethyl 2,6-dimethyl-4-{3'-[N-phenoxycarbonyl-1',6'-dihydropyridyl]}-1,4-dihydropyridine-3,5-dicarboxylate according to claim 1.

12. diethyl 2,6-dimethyl-4-{3'-[N-phenoxycarbonyl-1',2'-dihydropyridyl]}-1,4-dihydropyridine-3,5-dicarboxylate according to claim 1.

13. diethyl 2,6-dimethyl-4-{3'-[N-phenoxycarbonyl-1',6'-dihydropyridyl]}-1,4-dihydropyridine-3,5-dicarboxylate according to claim 1.

14. diisopropyl 2,6-dimethyl-4-{3'-[N-phenoxycarbonyl-1',2'-dihydropyridyl]}-1,4-dihydropyridine-3,5-dicarboxylate according to claim 1.

15. diisopropyl 2,6-dimethyl-4-{3'-[N-phenoxycarbonyl-1',6'-dihydropyridyl]}-1,4-dihydropyridine-3,5-dicarboxylate according to claim 1.

16. diisobutyl 2,6-dimethyl-4-{3'-[N-phenoxycarbonyl-1',2'-dihydropyridyl]}-1,4-dihydropyridine-3,5-dicarboxylate according to claim 1.

17. diisobutyl 2,6-dimethyl-4-{3'-[N-phenoxycarbonyl-1',6'-dihydropyridyl]}-1,4-dihydropyridine-3,5-dicarboxylate according to claim 1.

18. diethyl 2,6-dimethyl-4-{3'-[N-t-butoxycarbonyl-1',2'-dihydropyridyl]}-1,4-dihydropyridine-3,5-dicarboxylate according to claim 1.

19. diethyl 2,6-dimethyl-4-{3'-[N-t-butoxycarbonyl-1',6'-dihydropyridyl]}-1,4-dihydropyridine-3,5-dicarboxylate according to claim 1.

20. diisopropyl 2,6-dimethyl-4-{3'-[N-t-butoxycarbonyl-1',2'-dihydropyridyl]}-1,4-dihydropyridine-3,5-dicarboxylate according to claim 1.

21. diisopropyl 2,6-dimethyl-4-{3'-[N-t-butoxycarbonyl-1',6'-dihydropyridyl]}-1,4-dihydropyridine-3,5-dicarboxylate according to claim 1.

22. diisobutyl 2,6-dimethyl-4-{3'-[N-t-butoxycarbonyl-1',2'-dihydropyridyl]}-1,4-dihydropyridine-3,5-dicarboxylate according to claim 1.

23. diisobutyl 2,6-dimethyl-4-{3'-[N-t-butoxycarbonyl-1',6'-dihydropyridyl]}-1,4-dihydropyridine-3,5-dicarboxylate according to claim 1.

24. 3-isobutyl-5-methyl 2,6-dimethyl-4-{3'-[N-methoxycarbonyl-1',2'-dihydropyridyl]}-1,4-dihydropyridine-3,5-dicarboxylate according to claim 1.

25. 3-isobutyl-5-methyl 2,6-dimethyl-4-{3'-[N-methoxycarbonyl-1',6'-dihydropyridyl]}-1,4-dihydropyridine-3,5-dicarboxylate according to claim 1.

26. 3-isobutyl-5-methyl 2,6-dimethyl-4-{3'-[N-phenoxycarbonyl-1',2'-dihydropyridyl]}-1,4-dihydropyridine-3,5-dicarboxylate according to claim 1.

27. 3-isobutyl-5-methyl 2,6-dimethyl-4-{3'-[N-phenoxycarbonyl-1',6'-dihydropyridyl]}-1,4-dihydropyridine-3,5-dicarboxylate according to claim 1.

28. 3-isopropyl-5-methyl 2,6-dimethyl-4-{3'-[N-t-butoxycarbonyl-1',2-dihydropyridyl]}-1,4-dihydropyridine-3,5-dicarboxylate according to claim 1.

29. 3-isopropyl-5-methyl 2,6-dimethyl-4-{3'-[N-t-butoxycarbonyl-1',6'-dihydropyridyl]}-1,4-dihydropyridine-3,5-dicarboxylate according to claim 1.

30. 3-methyl 5-cyano-2,6-dimethyl-4-{3'-[N-methoxycarbonyl-1',2'-dihydropyridyl]}-1,4-dihydropridine-3-carboxylate according to claim 1.

31. 3-methyl 5-cyano-2,6-dimethyl-4-{3'-[N-methoxycarbonyl-1',6'-dihydropyridyl]}-1,4-dihydropyridine-3-carboxylate according to claim 1.

32. 3-methyl 5-cyano-2,6-dimethyl-4-{3'-[N-phenoxycarbonyl-1',2'-dihydropyridyl]}-1,4-dihydropyridine-3-carboxylate according to claim 1.

33. 3-methyl 5-cyano-2,6-dimethyl-4-{3'-[N-phenoxycarbonyl-1',6'-dihydropyridyl]}-1,4-dihydropyridine-3-carboxylate according to claim 1.

34. 3,5-dicyano-2,6-dimethyl-4-{3'-[N-methoxycarbonyl-1',2'-dihydropyridyl]}-1,4-dihydropyridine according to claim 1.

35. 3,5-dicyano-2,6-dimethyl-4-{3'-[N-methoxycarbonyl-1',6'-dihydropyridyl]}-1,4-dihydropyridine according to claim 1.

36. 3,5-dicyano-2,6-dimethyl-4-{3'-[N-phenoxycarbonyl-1',2'-dihydropyridyl]}-1,4-dihydropyridine according to claim 1.

37. 3,5-dicyano-2,6-dimethyl-4-{3'-[N-phenoxycarbonyl-1',6'-dihydropyridyl]}-1,4-dihydropyridine according to claim 1.

38. 3,5-dicyano-2,6-dimethyl-4-{3'-[N-t-butoxycarbonyl-1',2'-dihydropyridyl]}-1,4-dihydropyridine according to claim 1.

39. 3,5-dicyano-2,6-dimethyl-4-{3'-[N-t-butoxycarbonyl-1',6'-dihydropyridyl]}-1,4-dihydropyridine according to claim 1.

40. dimethyl 2,6-dimethyl-4-[4'-(N-methoxycarbonyl-1',2'-dihydropyridyl)]-1,4-dihydropyridine-3,5-dicarboxylate according to claim 1.

41. diethyl 2,6-dimethyl-4-[4'-(N-methoxycarbonyl-1',2'-dihydropyridyl)]-1,4-dihydropyridine-3,5-dicarboxylate according to claim 1.

42. diisobutyl 2,6-dimethyl-4-[4'-(N-methoxycarbonyl-1',2'-dihydropyridyl)]-1,4-dihydropyridine-3,5-dicarboxylate according to claim 1.

43. dimethyl 2,6-dimethyl-4-[4'-(N-phenoxycarbonyl-1',2'-dihydropyridyl)]-1,4-dihydropyridine-3,5-dicarboxylate according to claim 1.

44. diethyl 2,6-dimethyl-4-[4'-(N-phenoxycarbonyl-1',2'-dihydropyridyl)]-1,4-dihydropyridine-3,5-dicarboxylate according to claim 1.

45. diisobutyl 2,6-dimethyl-4-[4'-(N-phenoxycarbonyl-1',2'-dihydropyridyl)]-1,4-dihydropyridine-3,5-dicarboxylate according to claim 1.

46. diethyl 2,6-dimethyl-4-[4'-(N-t-butoxycarbonyl-1',2'-dihydropyridyl)]-1,4-dihydropyridine-3,5-dicarboxylate according to claim 1.

47. diisobutyl 2,6-dimethyl-4-[4'-(N-t-butoxycarbonyl-1',2'-dihydropyridyl)]-1,4-dihydropyridine-3,5-dicarboxylate according to claim 1.

48. 3,5-dicyano-2,6-dimethyl-4-[4'-(N-methoxycarbonyl-1',2'-dihydropyridyl)]-1,4-dihydropyridine according to claim 1.

49. 3-isobutyl-5-methyl 2,6-dimethyl-4-[4'-(N-methoxycarbonyl-1',2'-dihydropyridyl)]-1,4-dihydropyridine-3,5-dicarboxylate according to claim 1.

50. 3-isobutyl-5-methyl 2,6-dimethyl-4-[4'-(N-phenoxycarbonyl-1',2'-dihydropyridyl)]-1,4-dihydropyridine-3,5-dicarboxylate according to claim 1.

51. 3-isopropyl-5-methyl 2,6-dimethyl-4-[4'-(N-t-butoxycarbonyl-1',2'-dihydropyridyl)]-1,4-dihydropyridine-3,5-dicarboxylate according to claim 1.

52. 3-isobutyl-5-methyl 2,6-dimethyl-4-[4'-(N-t-butoxycarbonyl-1',2'-dihydropyridyl)]-3,5-dicarboxylate according to claim 1.

53. dimethyl 2,6-dimethyl-4-[2'-(N-methyl-1',2',3',6'-tetrahydropyridyl)]-1,4-dihydropyridine-3,5-dicarboxylate according to claim 1.

54. diethyl 2,6-dimethyl-4-[2'-(N-methyl-1',2',3',6'-tetrahydropyridyl)]-1,4-dihydropyridine-3,5-dicarboxylate according to claim 1.

55. dimethyl 2,6-dimethyl-4-[4'-(N-methyl-1',2',3',6'-tetrahydropyridyl)]-1,4-dihydropyridine-3,5-dicarboxylate according to claim 1.

56. diethyl 2,6-dimethyl-4-[4'-(N-methyl-1',2',3',6'-tetrahydropyridyl)]-1,4-dihydropyridine-3,5-dicarboxylate according to claim 1.

57. dimethyl 2,6-dimethyl-4-[5'-(N-methyl-1',2',3',6'-tetrahydropyridyl)]-1,4-dihydropyridine-3,5-dicarboxylate according to claim 1.

58. diethyl 2,6-dimethyl-4-[5'-(N-methyl-1',2',3',6'-tetrahydropyridyl)]-1,4-dihydropyridine-3,5-dicarboxylate according to claim 1.

59. A composition comprising the compound of claim 1 and a pharmaceutically acceptable carrier, wherein sufficient active compound is present so that the composition has antihypertensive, antiarrhythmic, vasodilating or negative inotropic activity.

60. The composition of claim 59, wherein the pharmaceutically acceptable carrier is a liquid carrier suitable for injection.

61. The composition of claim 59, wherein the pharmaceutically acceptable carrier is a solid or suitable liquid for oral administration.

* * * * *